United States Patent
Tobe et al.

(10) Patent No.: US 7,358,403 B2
(45) Date of Patent: Apr. 15, 2008

(54) CHIRAL SENSOR

(75) Inventors: Yoshito Tobe, Ashiya (JP); Keiji Hirose, Osaka (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 325 days.

(21) Appl. No.: 10/525,012

(22) PCT Filed: Jun. 10, 2003

(86) PCT No.: PCT/JP03/07313

§ 371 (c)(1),
(2), (4) Date: Feb. 17, 2005

(87) PCT Pub. No.: WO2004/018447

PCT Pub. Date: Mar. 4, 2004

(65) Prior Publication Data

US 2005/0227366 A1 Oct. 13, 2005

(30) Foreign Application Priority Data

Aug. 20, 2002 (JP) .............................. 2002-239777

(51) Int. Cl.
*C07C 43/32* (2006.01)
(52) U.S. Cl. .................. 568/662; 436/164; 436/172
(58) Field of Classification Search ................ 436/164, 436/172; 564/504; 568/679, 662
See application file for complete search history.

(56) References Cited

OTHER PUBLICATIONS

Nakashima, Kenichiro et al., Talanta, 1984, vol. 31, No. 9, pp. 749-751.*
Dolman, Mark et al.; Chromogenic Reagents, 1996, Analyst, vol. 121, pp. 1777.*
Reichardt, Christian et al.; Pyridinum N-Phenolate Betaine dyes and Their Application to the Characterization of Polarity of solvents, XXII. 1997, vol. 4 pp. 709.*
Zhang et al., Chem. Rev., vol. 97, pp. 3313-3361 (1997).
Keiji Hirose, J. Incl. Phenom. and Macrocyclic Chem., vol. 39, pp. 193-209, (2001).
Lin et al., J. Am. Chem. Soc., vol. 124, No. 10, pp. 2088-2089 (2002).
Tian Jun Liu et al., Chirality, vol. 13, pp. 595-600, (2001).
Wang et al., Chem. Commun., pp. 1747-1748 (1998).
Pu et al., Angew. Chem. Int. Ed., vol. 39. No. 20, pp. 3638-3641, (2000).
Tanigawa, Isamu et al., Tetrahedron Letters, 1984, vol. 25, No. 46, pp. 5327 to 5330.
Naskashima, Ken'ichiro et al., Bulletin of the Chemical Society of Japan, 1987, vol. 60, No. 9, pp. 3219 to 3223.
Nakashima, Ken'ichiro et al., Talanta, 1984, vol. 31, No. 9, pp. 749 to 751.
Wang, Defen et al., Gaodeng Xuexiao Huaxue Xuebao, 1985, vol. 6, No. 1, pp. 45 to 48.
Tsubaki, Kazunori et al., Organic Letters, 2001, vol. 3, No. 25, pp. 4071 to 4073.
Gong et al., J. Org. Chem. vol. 66, pp. 2358-2367, (2001).
K. Hirose et al., Tetrahedron: Asymmetry, vol. 14, No. 5, Mar. 7, 2003, pp. 555-566.
K. Hirose et al., Tetrahedron Letters, vol. 43, No. 7, Nov. 18, 2002, pp. 8539-8542.

* cited by examiner

*Primary Examiner*—Yvonne Eyler
*Assistant Examiner*—Yate' K Cutliff
(74) *Attorney, Agent, or Firm*—Birch, Stewart, Kolasch & Birch, LLP

(57) ABSTRACT

An optically active compound having an unsaturated bond at an optically active binding site, wherein the unsaturated bond and a fluorescent substituent or a substituent capable of imparting fluorescence are united in a conjugated manner; and a chiral sensor comprising the optically active compound as defined above. The chiral sensor can highly selectively recognize a specified chiral compound in high sensitivity.

2 Claims, No Drawings

CHIRAL SENSOR

This application is the national phase of PCT/JP03/07313, filed on Jun. 10, 2003 which claims priority on Japanese Patent Application No. 2002-239777 filed on Aug. 20, 2002. The entire contents of these applications are hereby incorporated by reference.

TECHNICAL FIELD

The present invention relates to an optically active compound and a chiral sensor comprising the compound. More specifically, the present invention relates to an optically active compound capable of recognizing a chiral compound in a high sensitivity and a chiral sensor comprising the compound. The chiral sensor is useful in separation or sensing in connection with its relationship with physiological activities for amines, amino acids and amino alcohols, sensing for the detection of a narcotic drug and the designation of the producing district, or the like.

BACKGROUND ART

Medicaments having optical isomers have been required to be developed as optical pure compounds from the viewpoint of adverse actions or the like. Therefore, the significance of optical resolution and examination of optical purity has been becoming increasingly high.

Especially, optically active amines such as ethanolamine derivatives and catecholamine derivatives have physiological activities for the central nervous system, and are important compounds as numerous medicament intermediates. Therefore, conventionally, numerous studies have been made on the complexation for recognizing enantiomers on the bases of host-guest interactions using crown ethers for optical resolution or analytical purposes of optically active amines [X. X. Zhang, J. S. Bradshaw, R. M. Izatt: *Chem. Rev.*, 97, 3313-3361 (1997): K. Hirose, *J. Incl. Phenom. and Macrocyclic Chem.*, 39, 193-209 (2001). and the like]. However, these complexes have low sensitivities, so that they are hardly used in practical purposes.

Chiral sensors which have been recently developed are those in a chain form containing binaphthol in the molecule (J. Lin, Q.-S. Hu, M.-H. Xu, L. Pu, *J. Am. Chem. Soc.*, 124, 2088-2089 (2002): J. L. Tian, J. C. Yong, S. Z. Ke, D. Wang, W. G. Da, Z. Y. Xiao, *Chirality*, 13, 595-600 (2001): D. Wang, T.-J. Liu, W.-C. Zhang, W. T. Slaven, C.-J. Li, *Chem. Commun.*, 1998, 1747-1748), and those having a dendrimer form (V. J. Pugh, Q.-S. Hu, L. Pu, *Angew. Chem. Int. Ed.*, 39, 3638-3641 (2000): L.-Z. Gong, Q.-S. Hu, L. Pu, *J. Org. Chem.*, 66, 2358-2367 (2001)). When these chiral sensors are used, the sensors have high sensitivities utilizing fluorescence emission. However, these chiral sensors do not have selectors (binding sites) which are easily prepared and have high selectivity, so that these sensors are hardly used in practical purposes.

In addition, most of the natural amino acids and the physiologically active substances are chiral compounds. However, under the current situation, the development of sensors capable of rapidly recognizing these chiral compounds in high sensitivity have been earnestly desired. This development is based on the fact that it is very difficult to satisfy high binding property and high selectivity against an enantiomer target of a receptor, in the conventional sensors.

DISCLOSURE OF INVENTION

An object of the present invention is to provide a practically very useful chiral sensor capable of recognizing with high selectivity a specified chiral compound in a high sensitivity.

The present invention relates to:

[1] an optically active compound having an unsaturated bond at an optically active binding site, wherein the unsaturated bond and a fluorescent substituent or a substituent capable of imparting fluorescence are united in a conjugated manner; and

[2] a chiral sensor comprising the optically active compound as defined above.

BEST MODE FOR CARRYING OUT THE INVENTION

The present inventors have prepared numerous optically active crown ethers having a pseudo-18-crown-6 framework, and performed studies on the formation of complexes for recognizing enantiomers in the solution. As a result, they have successfully developed a phenolic crown ether having a high enantioselectivity especially for ethanolamine derivatives. This compound has features that ① the compound can be prepared from a commercially available, inexpensive chiral compound, that ② the compound has a phenol moiety (acidic), so that the compound binds with a neutral amine to form a salt-complex, that ③ the absorption spectrum changes with the formation of the salt-complex, and the like.

Numerous compounds were prepared, and the position of a chiral center and the substituent of the chiral center of the crown ether ring have been optimized. As a result, it has been found that a host molecule 1 in the formula:

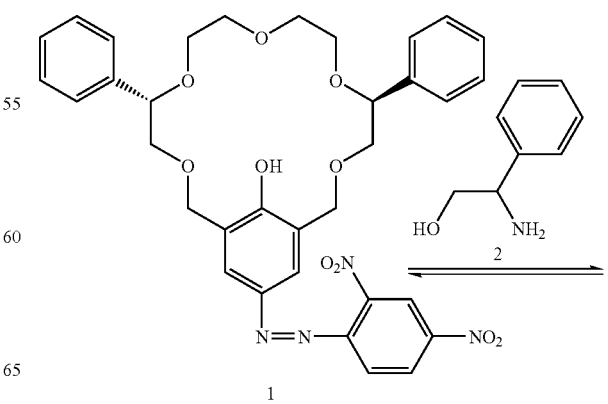

-continued

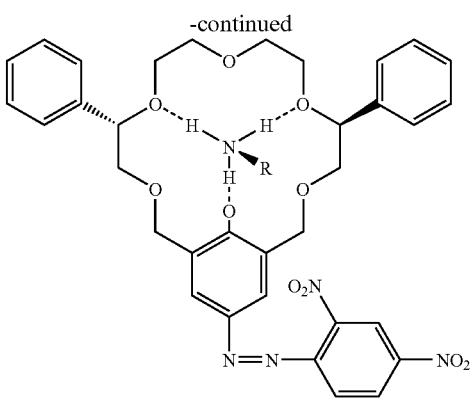

3

R = CHPh(CH₂OH)

is excellent in all the features. The host molecule 1 forms a salt-complex 3 with an amino alcohol 2.

In this example, the R/S ratio of the complex stability constant at room temperature reaches 13-folds. The high enantioselectivity of this host molecule 1 is reflected in a great difference in the absorption spectrum based on a phenolate salt-complex near 560 nm in the visible absorption spectrum.

While the present inventors pursued the studies for further improving the selectivity, the host for recognizing enantiomers has been developed for practical use. As a result, when a chiral selector represented by the formula:

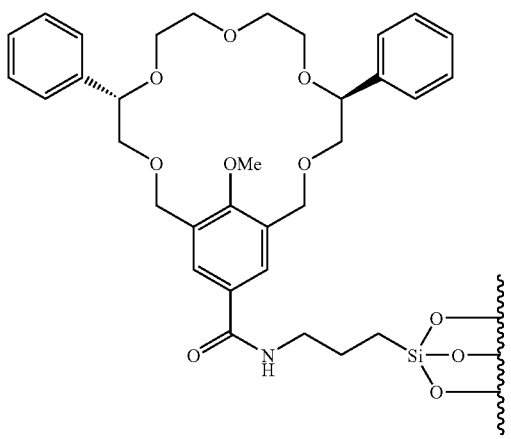

is applied to chromatography for separation of optical isomers, the practical use as a chemically bonded type optically active column has been successfully accomplished for the first time in the world. This chiral selector has a sufficiently high enantiomer-recognizing ability as a chiral selector for the optically active column.

As described above, there have been verified that the pseudo-18-crown-6 type host compound has a very high enantiomer-recognizing ability, and that its cost is bearable for practical purposes by optimizing the chiral site.

Next, the present inventors have considered that the development of measures for improving enantiomer-recognizing ability based on a new principle is required in order that an analyte is detected in an even higher sensitivity, and that the selectivity is further enhanced. Therefore, they have remarked on the fluorescence spectrum.

In general, fluorescent host compounds have been developed and applied to microanalysis by utilizing the excellent sensitivity. The present inventors have developed a fluorescent new host having selectivity amplifying effects by skillfully utilizing the feature of emission property and equilibrium reaction of host-guest complexation in addition to the high sensitivity of the fluorescent host compound.

This compound is an optically active compound having an unsaturated bond at an optically active binding site, wherein the unsaturated bond and a fluorescent substituent or a substituent capable of imparting fluorescence are united in a conjugated manner. This compound is useful as a chiral sensor.

Representative examples of the above-mentioned optically active compound include a compound represented by the formula (I):

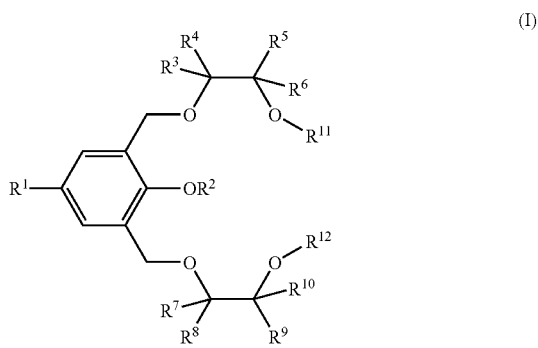

(I)

wherein $R^1$ is an aromatic group or an aromatic ethynyl group; $R^2$ is a hydrogen atom or an alkyl group having 1 to 10 carbon atoms; each of $R^3$, $R^4$, $R^5$, $R^6$, $R^7$, $R^8$, $R^9$ and $R^{10}$ is independently a hydrogen atom, or an alkyl group having 1 to 30 carbon atoms, a cyclic alkyl group having 3 to 30 carbon atoms or an aryl group having 6 to 30 carbon atoms, each of which may have a substituent, with proviso that each of $R^4$ and $R^5$, and $R^8$ and $R^9$ may be bonded to form an alkylene group having 2 to 60 carbon atoms; and each of $R^{11}$ and $R^{12}$ is independently a hydrogen atom or an alkyl group having 1 to 15 carbon atoms which may have a hetero-atom, with proviso that $R^{11}$ and $R^{12}$ may be bonded to form an alkylene group having 2 to 30 carbon atoms which may have a hetero-atom.

In the formula (I), $R^1$ is an aromatic group or an aromatic ethynyl group.

The aromatic group includes, for instance, an aryl group having 6 to 20 carbon atoms, preferably 6 to 16 carbon atoms, such as a phenyl group, a tolyl group, a xylyl group, a biphenyl group, a naphthyl group, an anthryl group, a phenanthryl group, and a pyrenyl group; an aryl group having 6 to 20 carbon atoms, preferably 6 to 16 carbon atoms, having a hetero-atom, such as a benzothiazolyl group and a naphthothiazolyl group; and the like. Among them, a naphthyl group, an anthryl group, a phenanthryl group, a pyrenyl group and a benzothiazolyl group are preferred.

The aromatic ethynyl group includes, for instance, an arylethynyl group having 8 to 22 carbon atoms, preferably 8 to 18 carbon atoms, such as a phenylethynyl group, a tolylethynyl group, a xylylethynyl group, a biphenylethynyl group, a naphthylethynyl group, an anthrylethynyl group, a phenanthrylethynyl group, and a pyrenylethynyl group; an arylethynyl group having 8 to 22 carbon atoms, preferably 8 to 18 carbon atoms, having a hetero-atom, such as a benzothiazolylethynyl group and a naphthothiazolylethynyl group; and the like. Among them, a phenylethynyl group, a naphthylethynyl group, an anthrylethynyl group, a phenanthrylethynyl group, a pyrenylethynyl group and a benzothiazolylethynyl group are preferred.

$R^2$ is a hydrogen atom or an alkyl group having 1 to 10 carbon atoms. Among them, a hydrogen atom and a methyl group are preferable.

Each of $R^3$, $R^4$, $R^5$, $R^6$, $R^7$, $R^8$, $R^9$ and $R^{10}$ is independently a hydrogen atom, or an alkyl group having 1 to 30 carbon atoms, a cyclic alkyl group having 3 to 30 carbon atoms or an aryl group having 6 to 30 carbon atoms, each of which may have a substituent, with proviso that each of $R^4$ and $R^5$, and $R^8$ and $R^9$ may be bonded to form an alkylene group having 2 to 60 carbon atoms. The above-mentioned substituent includes, for instance, a hydroxyl group, a thiol group, an amino group, a nitro group, a halogen atom (for instance, a fluorine atom, a chlorine atom, a bromine atom, and an iodine atom), and the like. It is preferable that each of $R^3$, $R^4$, $R^5$, $R^7$, $R^8$ and $R^9$ is a hydrogen atom.

Examples of $R^6$ and $R^{10}$ include an aryl group having 6 to 30 carbon atoms, preferably 6 to 12 carbon atoms, such as a phenyl group and a 1-naphthyl group; and a cyclic alkyl group having 3 to 30 carbon atoms, preferably 3 to 10 carbon atoms, such as a 1-adamantyl group; and the like. Preferred examples of $R^6$ and $R^{10}$ include a phenyl group, a 1-naphthyl group, a 1-adamantyl group, a 1-(3,5-dimethyl)phenyl group and a 1-bi-2-naphthyl group, among which a phenyl group is preferable.

Each of $R^{11}$ and $R^{12}$ is independently a hydrogen atom or an alkyl group having 1 to 15 carbon atoms which may have a hetero-atom, with proviso that $R^{11}$ and $R^{12}$ may be bonded to form an alkylene group having 2 to 30 carbon atoms which may have a hetero-atom. The above-mentioned hetero-atom includes, for instance, an oxygen atom, a sulfur atom, nitrogen atom and the like. Preferred $R^{11}$ and $R^{12}$ include a group in which $R^{11}$ and $R^{12}$ are bonded to form a group represented by the formula:

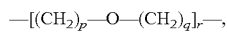

wherein each of p, q and r is independently an integer of from 1 to 15.

Among the above-mentioned optically active compounds, a preferred compound is a compound represented by the formula (III):

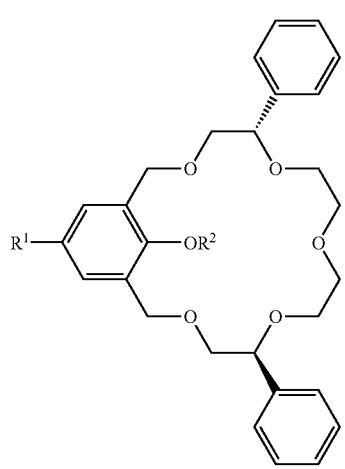

wherein $R^1$ and $R^2$ are as defined above, as representatively exemplified by the formula (II):

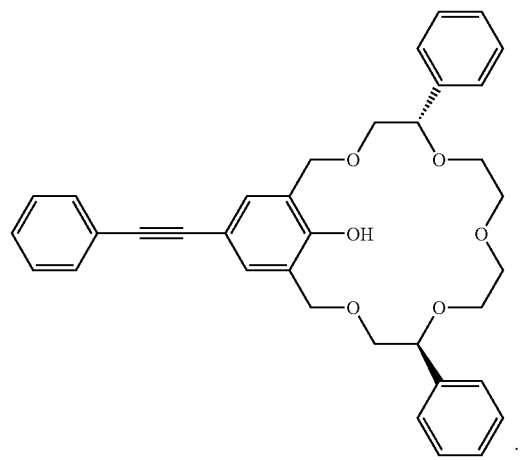

The basic structures of the compound represented by the formula (II) are phenolic pseudo-18-crown-6 hosts having two asymmetric carbon atoms, in which phenylacetylene is introduced into a para-position of the phenolic hydroxy group to make the host fluorescent, and at the same time the degree of acidity of the phenolic hydroxy group is adjusted to a level sufficient for forming a salt with an amine.

An important feature in the design of the optically active compound of the present invention resides in that the fluorescence emission band of the host overlaps with the absorption band of the complex.

Consequently, three quenching processes can be considered:

① quenching by complex formation in a ground state (static quenching);

② quenching by interaction in an excited state (dynamic quenching); and

③ quenching by reabsorption of the fluorescence emission of the host by the complex (reabsorption quenching)

The effect of ① mentioned above acts so that the enantioselectivity is always amplified, and the selectivity can be amplified by the effect of ② mentioned above.

In the optically active compound of the present invention, the compound represented by the formula (II) can be obtained, for instance, through eight steps from (S)-mandelic acid by the preparation route as described in the following scheme:

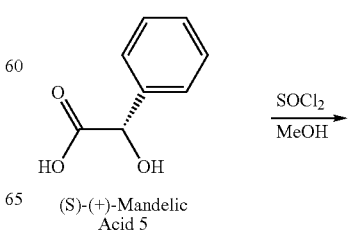

(S)-(+)-Mandelic Acid 5

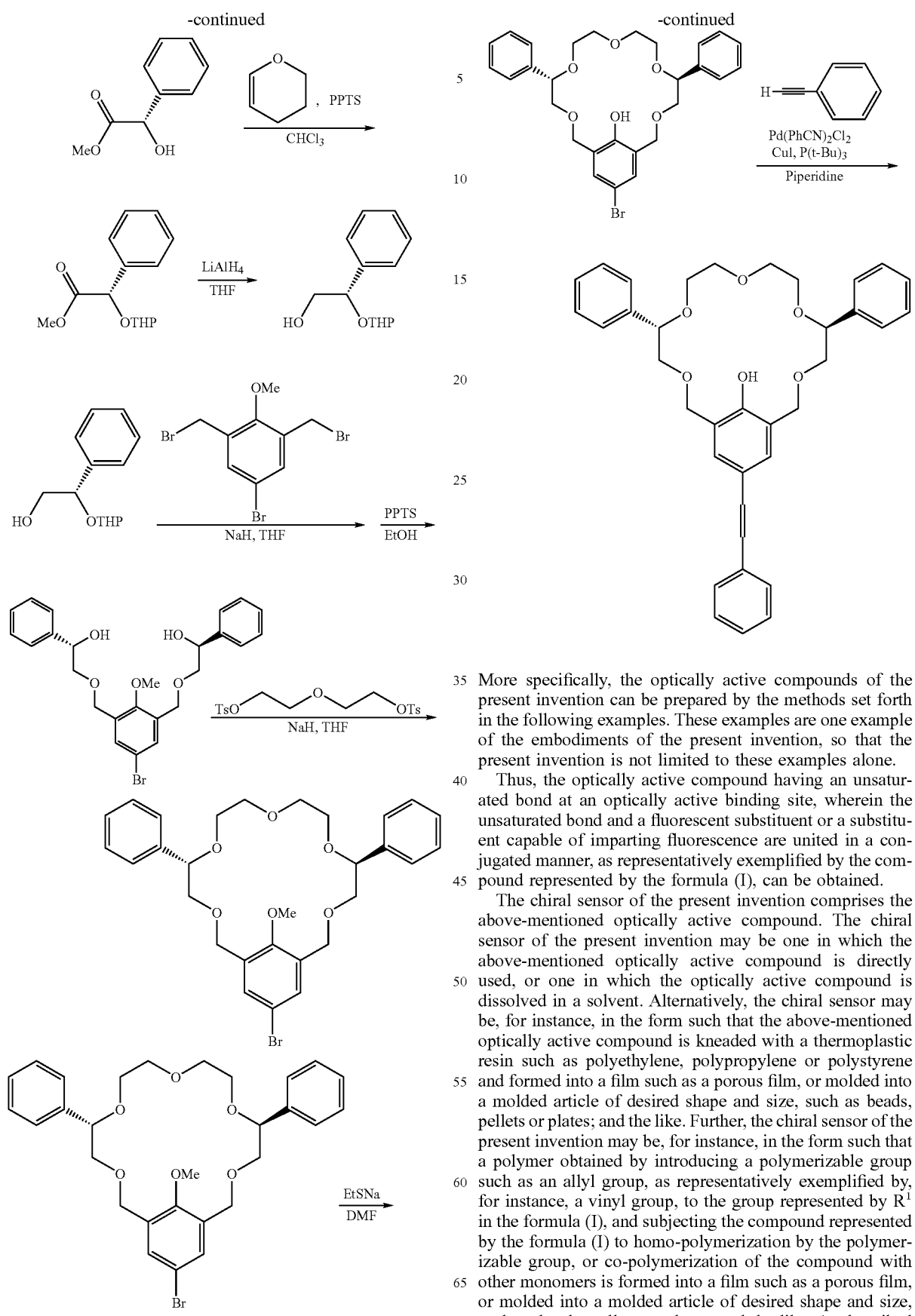

More specifically, the optically active compounds of the present invention can be prepared by the methods set forth in the following examples. These examples are one example of the embodiments of the present invention, so that the present invention is not limited to these examples alone.

Thus, the optically active compound having an unsaturated bond at an optically active binding site, wherein the unsaturated bond and a fluorescent substituent or a substituent capable of imparting fluorescence are united in a conjugated manner, as representatively exemplified by the compound represented by the formula (I), can be obtained.

The chiral sensor of the present invention comprises the above-mentioned optically active compound. The chiral sensor of the present invention may be one in which the above-mentioned optically active compound is directly used, or one in which the optically active compound is dissolved in a solvent. Alternatively, the chiral sensor may be, for instance, in the form such that the above-mentioned optically active compound is kneaded with a thermoplastic resin such as polyethylene, polypropylene or polystyrene and formed into a film such as a porous film, or molded into a molded article of desired shape and size, such as beads, pellets or plates; and the like. Further, the chiral sensor of the present invention may be, for instance, in the form such that a polymer obtained by introducing a polymerizable group such as an allyl group, as representatively exemplified by, for instance, a vinyl group, to the group represented by $R^1$ in the formula (I), and subjecting the compound represented by the formula (I) to homo-polymerization by the polymerizable group, or co-polymerization of the compound with other monomers is formed into a film such as a porous film, or molded into a molded article of desired shape and size, such as beads, pellets or plates; and the like. As described above, the chiral sensor of the present invention can be used in a wide range in various forms.

The chiral sensor of the present invention can be used, for instance, as a chiral sensor for a low-concentration substance requiring both high sensitivity and high selectivity by monitoring fluorescence emission in the absorption band of the complex in the long-wavelength side than the excitation light.

Since the chiral sensor of the present invention is capable of highly selectively recognizing a specified chiral compound in high sensitivity, the chiral sensor is very useful for practical purposes. For instance, the chiral sensor can be suitably used in separation or sensing in connection with its relationship with physiological activities for amines, amino acids and amino alcohols, sensing for the detection of a narcotic drug and the designation of the producing district or the like.

Next, the present invention will be described more specifically based on Examples, without intending to limit the present invention thereto.

Here, the spectroscopic devices used in the following Examples are as follows.

(a) NMR Spectrum: Nuclear Magnetic Resonance Spectrum one manufactured by JASCO Corporation, JEOL JNM-GSX-270

(b) IR Spectrum:

one manufactured by JASCO Corporation, JASCO Fourier transform infrared spectrophotometer FT/IR-410

(c) Optical Rotation:

one manufactured by JASCO Corporation, JASCO Digital Polarimeter

DIP-370

(d) Melting Point:

a hot plate equipped with a microscope (e) Mass Spectrum:

one manufactured by Shimadzu Corporation, SHIMADZU LCMS-2010

(f) Open Column Chromatography:

one manufactured by MERCK, Silica-gel 60 (70-230 mesh ASTM)

(g) Recycling High-Performance Liquid Chromatography:

one manufactured by Japan Analytical Industry Co., Ltd. (JAI), LC-908 20 mm JAUGEL-1H, 2H GPC (h) Thin-Layer Chromatography:

one manufactured by MERCK, Silica-gel 60 $F_{254}$

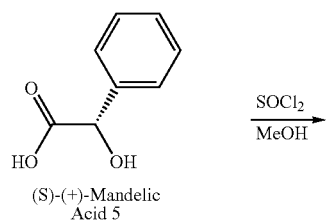

(S)-(+)-Mandelic Acid 5

-continued

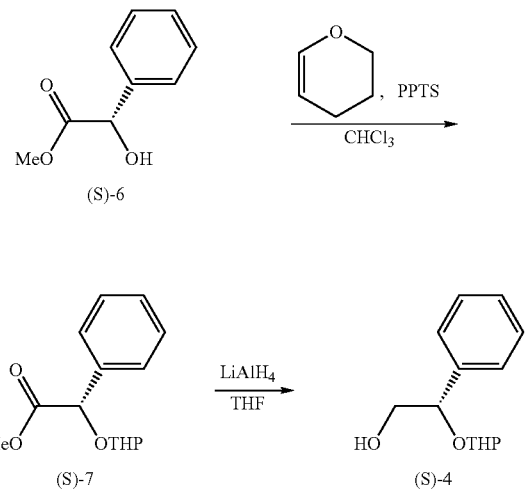

EXAMPLE 1

Preparation of Chiral Unit (S)-4

A 1-L three-neck flask was charged with methanol (300 mL, 7.41 mol) and (S)-(+)-mandelic acid 5 (50.2 g, 330 mmol) while stirring, and the mixture was cooled to 0° C. in an ice-salt bath. Thereafter, thionyl chloride (27.0 mL, 379 mmol) was gradually added dropwise thereto from a dropping funnel. After the termination of the dropwise addition, the temperature of the mixture was recovered to an ambient temperature, at which the mixture was stirred for 23 hours.

Next, excess thionyl chloride and methanol were distilled under reduced pressure. Thereafter, the residue was extracted with chloroform, and an organic layer was washed with water and with saturated brine, and the mixture obtained was dried over anhydrous magnesium sulfate, and thereafter concentrated, thereby giving methyl (S)-(+)-mandelate (S)-6 (47.5 g, 286 mmol) in the form of a white solid.

A 1-L eggplant-shaped flask equipped with a calcium chloride tube was charged with chloroform (700 mL) and methyl (S)-(+)-mandelate (S)-6 (47.3 g, 285 mmol), and thereafter dihydropyran (100 mL, 1.07 mol) was added thereto, while stirring for 40 minutes in an ice bath, and pyridinium p-toluenesulfonate (3.56 g, 14.2 mmol) was added thereto. The temperature of the mixture was recovered to room temperature, and the mixture was stirred for 3 hours. Thereafter, the mixture was washed with water and with saturated brine, and the mixture obtained was dried over anhydrous magnesium sulfate and concentrated, to give an yellowish oily crude product (S)-7 (93.9 g).

A 1-L three-neck flask was charged with anhydrous tetrahydrofuran (500 mL) under nitrogen gas stream, and the content was cooled to −20° C. in a dry ice-oil bath. Thereafter, lithium aluminum hydride (6.92 g, 182 mmol) was gradually added thereto.

Next, a solution prepared by dissolving the yellowish oily crude product (S)-7 (32.9 g) in anhydrous tetrahydrofuran (50 mL) was gradually added dropwise to the above-mentioned solution over a period of 1 hour, and the mixture was stirred at room temperature for 3 hours. Thereafter, the mixture obtained was again cooled to −20° C. in the dry ice-oil bath, and acetone (45 mL) was added thereto to stop the reaction.

After the solution was stirred overnight, this solution was subjected to suction filtration, and each of a solid portion and a filtrate portion was extracted with hexane-ethyl acetate. The organic layer was washed with saturated brine. Thereafter, the mixture obtained was dried over anhydrous magnesium sulfate, and concentrated, to give (S)-4 (24.9 g, 112 mmol) in the form of a pale yellowish oily product (yield: 97%).

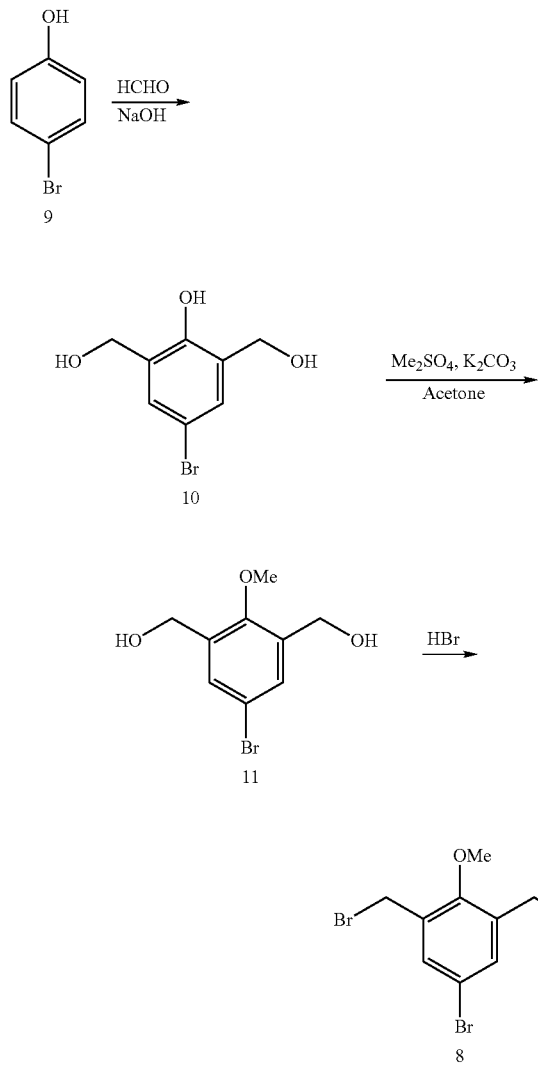

EXAMPLE 2

Preparation of Tribromide 8

A 3-L Erlenmeyer flask shielded by covering the flask with an aluminum foil was charged with sodium hydroxide (135 g, 3.27 mol) and water (540 mL), while cooling, and the contents were completely dissolved. p-Bromophenol (508 g, 2.85 mol) was added thereto and completely dissolved. The temperature of the mixture was recovered to room temperature, a 37% aqueous formaldehyde solution (1200 mL, 16.1 mol) was added thereto, and the mixture was allowed to stand for 12 days. The mixture was cooled in an ice bath, and a 3 N sulfuric acid was added dropwise thereto while thoroughly stirring the mixture with a mechanical stirrer. The precipitated solid obtained by allowing the mixture to stand for 5 hours was subjected to suction filtration, and the residue was washed with water, and air-dried, to give a crude product (848 g) of a triol form 10.

A 3-L three-neck flask was charged with acetone (2 L), potassium carbonate (100 g, 720 mmol), a product (103 g) prepared by pulverizing the crude triol product 10 obtained above, and dimethyl sulfate (43.0 mL, 431 mmol). The contents were refluxed with heating for 3 hours, while warming with a hot water bath at 60° C. The temperature of the mixture was recovered to room temperature, and thereafter, water (500 mL) was added thereto. Acetone was distilled off under reduced pressure with a rotary evaporator. The precipitated solid was subjected to suction filtration, washed with water, and then air-dried, to give a compound 11 (117 g).

A 3-L three-neck flask containing a 48% aqueous hydrogen bromide (2 L) was charged with the resulting compound 11 (59.2 g). The mixture was stirred for 4 hours with a mechanical stirrer while warming the mixture at 60° C. The temperature of the mixture was recovered to room temperature, and water (500 mL) was added thereto. The precipitated beige color solid was subjected to suction filtration. The residue was dissolved in a proper amount of chloroform, and the solution was filtered in a silica gel, and concentrated, thereby giving a tribromide 8 (53.3 g, 142 mmol) in the form of a white solid (yield: 73%).

$^1$H-NMR (270 MHz, CDCl$_3$, 30° C.) δ: 4.00 ppm (3H, s, OMe), 4.48 (4H, s, benzyl), 7.49 (2H, s, ArH)

EXAMPLE 3

Preparation of Diethylene Glycol Ditosylate 12

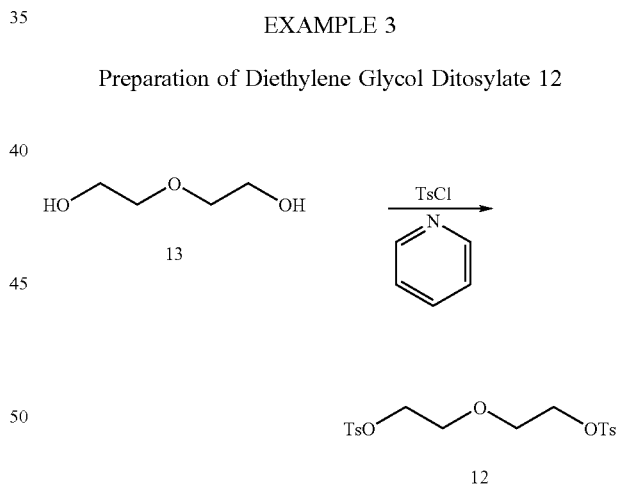

A 500 mL eggplant-shaped flask was charged with diethylene glycol 13 (15.0 mL, 155 mmol) and pyridine (300 mL), and p-toluenesulfonyl chloride (68.0 g, 351 mmol) was gradually added thereto in an ice bath. The mixture was stirred for 4 hours in the ice bath. Thereafter, a 1-L Erlenmeyer flask containing ice was charged with the reaction solution, and a concentrated hydrochloric acid (220 mL) was added thereto in the ice bath to adjust its pH to 4. The reaction mixture was subjected to suction filtration, and thereafter the residue was dissolved in chloroform. The mixture obtained was dried over anhydrous magnesium sulfate and concentrated, to give a product 12 (54.4 g, 131 mmol) in the form of a white solid (yield: 85%).

$^1$H-NMR (270 MHz, CDCl$_3$, 30° C.) δ: 2.45 ppm (6H, s, CH$_3$), 3.61 (4H, t, —CH$_2$—), 4.10 (4H, t, —CH$_2$—), 7.34 (4H, d, J=8.3 Hz, ArH), 7.78 (4H, d, J=8.3 Hz, ArH)

EXAMPLE 4

Preparation of Diol Form (S,S)-14

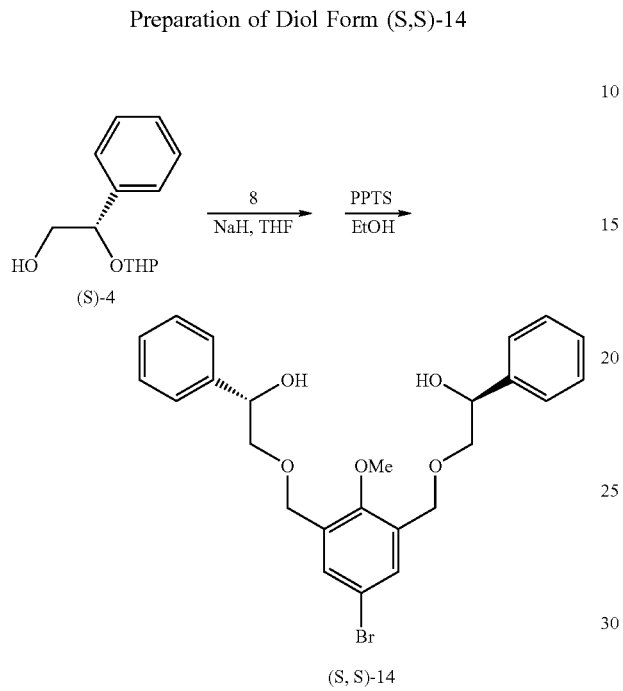

A 1-L three-neck flask was charged with anhydrous tetrahydrofuran (250 mL) and 60% sodium hydride (5.41 g, 135 mmol) under a nitrogen gas stream. A solution prepared by dissolving (S)-4 (19.1 g, 85.9 mmol) in anhydrous tetrahydrofuran (130 mL) was added dropwise thereto over a period of 1 hour. The mixture was refluxed at 60° C. for 30 minutes, and thereafter a solution prepared by dissolving the compound 8 in anhydrous tetrahydrofuran (130 mL) (12.2 g, 32.7 mmol) was added dropwise thereto over a period of 1.5 hours. The mixture obtained was stirred overnight in this state. Heating was stopped, and water (20 mL) was gradually added dropwise thereto in an ice bath to terminate the reaction. Thereafter, the solution was concentrated under reduced pressure. This residue was extracted with hexane-ethyl acetate, and the organic layer was washed with saturated brine. Thereafter, the mixture obtained was dried over anhydrous magnesium sulfate and concentrated, to give a reddish brown oily product (26.8 g).

This formed product was transferred to a 500 mL eggplant-shaped flask equipped with a calcium chloride tube. The flask was charged with ethanol (130 mL) and pyridinium p-toluenesulfonate (1.14 g, 4.54 mmol), and the mixture was stirred at 50° C. for 4 days. The solvent was concentrated under reduced pressure, and thereafter the concentrate was purified by silica gel column chromatography (hexane-ethyl acetate), thereby giving a product (S,S)-14 (13.3 g, 27.8 mmol) in the form of a yellowish oily product (yield: 85%). $^1$H-NMR (270 MHz, CDCl$_3$, 30° C.) δ: 3.56 ppm (2H, dd, J=8.5, 9.5 Hz, —CH$_2$—), 3.69 (2H, dd, J=3.5, 9.5 Hz, —CH$_2$—), 3.73 (3H, s, OCH$_3$), 4.60 (4H, s, benzyl), 4.94 (2H, dd, J=3.5, 8.5 Hz, methine), 7.28-7.40 (10H, m, Ph), 7.48 (2H, s, ArH)

EXAMPLE 5

Preparation of Crown Ether (S,S)-15

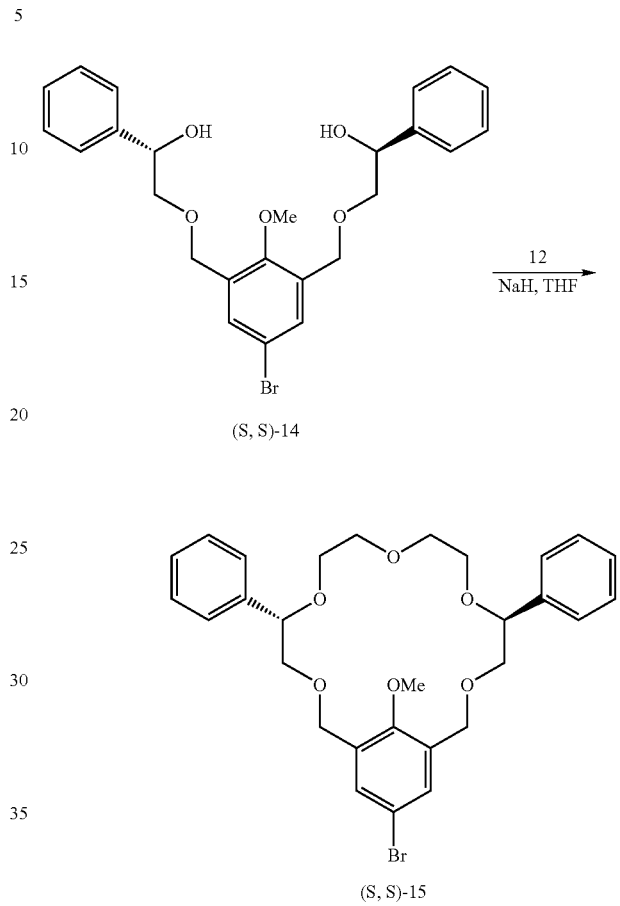

A 2-L three-neck flask was charged with 60% sodium hydride (3.57 g, 89.1 mmol) under a nitrogen gas stream, and the paraffin was washed out with hexane. Anhydrous tetrahydrofuran (800 mL) was added thereto, and the mixture was refluxed with heating. A mixed solution prepared by dissolving the compound 12 (6.52 g, 15.7 mmol) and the product (S,S)-14 (7.38 g, 15.4 mmol) in anhydrous tetrahydrofuran (100 mL) was added dropwise thereto over a period of 19 hours using a dropping funnel equipped with a needle. The mixture was heated at 65° C. for 22 hours, and thereafter water (50 mL) was added dropwise thereto in an ice bath to stop the reaction. The solution was concentrated under reduced pressure, and thereafter the residue was extracted with hexane-ethyl acetate. The organic layer was washed with saturated brine, and thereafter the mixture obtained was dried over anhydrous magnesium sulfate and concentrated, to give a reddish brown oily product (7.44 g). The product obtained was purified by silica gel column chromatography (hexane-ethyl acetate), thereby giving a product (S,S)-15 (2.21 g, 3.96 mmol) in the form of a white bubbly solid (yield: 26%).

$^1$H-NMR (270 MHz, CDCl$_3$, 30° C.) δ: 3.42-3.68 ppm (12H, m, —OCH$_2$—), 4.26 (3H, s, OCH$_3$), 4.52 (2H, d, J=8.6 Hz, methine), 4.44, 4.69 (4H, AB, J=10.0 Hz, benzyl), 7.28-7.37 (10H, m, Ph), 7.42 (2H, s, ArH)

EXAMPLE 6

Preparation of Crown Ether (S,S)-3

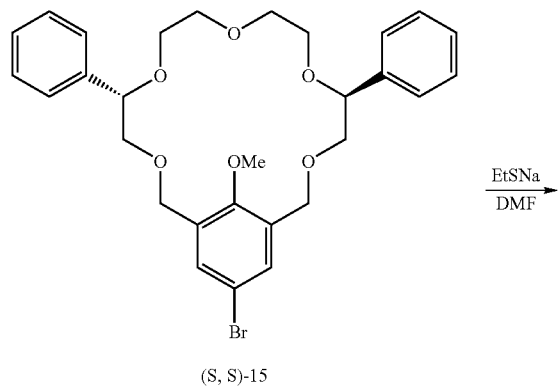

EXAMPLE 7

Preparation of Crown Ether (S,S)-2

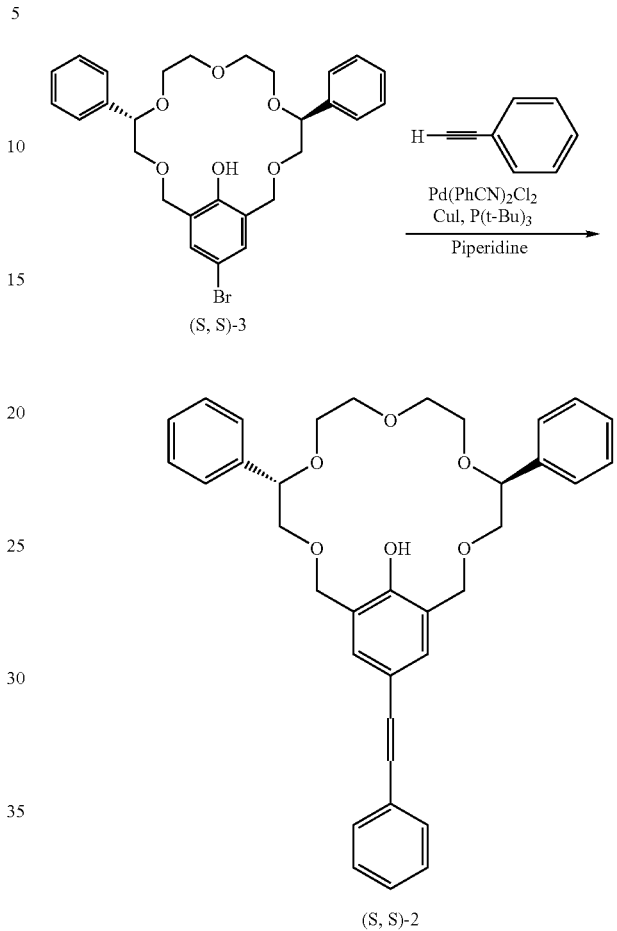

Inside a draft, a 300 mL three-neck flask was charged with anhydrous dimethylformamide (70 mL) under a nitrogen gas stream, and the content was cooled in an ice bath. Thereafter, 60% sodium hydride (1.79 g, 44.7 mmol) was added thereto while stirring, and ethanethiol (7.0 mL, 92 mmol) was added dropwise thereto from a syringe. Next, a solution prepared by dissolving the product (S,S)-15 (1.90 g, 3.42 mmol) in anhydrous dimethylformamide (30 mL) was added dropwise to the mixture over a period of 1 hour, and thereafter the mixture was stirred at 80° C. for 1 hour. Next, water (10 mL) was added thereto in the ice bath to stop the reaction, and 6 N hydrochloric acid was added to the mixture obtained to neutralize the mixture. Thereafter, the mixture obtained was extracted with chloroform. The organic layer was washed sequentially with an aqueous solution of Antiformin and with saturated brine. The mixture obtained was dried over anhydrous magnesium sulfate and concentrated to give a brown oily product. The resulting product was purified by silica gel column chromatography (hexane-ethyl acetate), and then purified by recycling high-performance column chromatography, thereby giving a product (S,S)-3 (1.32 g, 2.43 mmol) (yield: 71%).

$^1$H-NMR (270 MHz, CDCl$_3$, 30° C.) δ: 3.55-3.80 ppm (12H, m, —OCH$_2$—), 4.65 (2H, dd, J=3.1, 8.5 Hz, methine), 4.73 (4H, s, benzyl), 7.29-7.38 (12H, m, Ph, ArH)

A 30 mL three-neck flask was equipped with septum and a ball condenser, and flame-dried under a nitrogen gas stream. The flask was equipped with a thermometer, and charged with copper (I) iodide (4.28 mg, 21.8 μmol) and dichlorobis(benzonitrile)palladium (II) (32.6 mg, 28.2 μmol), and the atmosphere was replaced with argon. The product (S,S)-3 (505 mg, 929 μmol), piperidine (5 mL) and tri-t-butylphosphine (20.0 μL, 73.8 μmol) were added thereto, and freeze-degassing was carried out. A solution prepared by dissolving phenylacetylene (125 μL, 1.11 mmol) in piperidine (1 mL) was added dropwise thereto, and the mixture was stirred for 4 hours at 40° C. Additional phenylacetylene (50 μL, 443 μmol) was added, and the mixture was stirred for additional 2 hours. Water (10 mL) was added in an ice bath to stop the reaction. The reaction solution was extracted with ether. The organic layer was washed sequentially with 0.1 N aqueous ammonium chloride solution, and with saturated brine. The mixture obtained was dried over anhydrous magnesium sulfate and concentrated. Thereafter, the concentrate was purified sequentially by silica gel column chromatography (hexane-chloroform), and recycling high-performance liquid column chromatography, to give a product (S,S)-2 (298 mg, 528 μmol) in the form of a beige color solid (yield: 57%).

$^1$H-NMR (270 MHz, CDCl$_3$, 30° C.) δ: 3.55-3.82 ppm (12H, m, —OCH$_2$—), 4.67 (2H, dd, J=3.0, 8.6 Hz, methine), 4.76 (4H, s, benzyl), 7.25-7.39 (12H, m, ArH), 7.44-7.49 (2H, m, ArH), 8.40 (1H, s, OH) $^{13}$C-NMR (67.5 MHz, CDCl$_3$, 30° C.) δ: 156.0 ppm (4°), 138.5 (4°), 132.9 (3°), 131.3 (3°), 128.4 (3°), 128.2 (3°), 128.0 (3°), 127.7 (3°), 126.8 (3°), 124.8 (4°), 123.6 (4°), 114.0 (4°), 89.3 (4°), 87.8 (4°), 81.4 (3°), 75.0 (2°), 70.6 (2°), 70.4 (2°), 69.0 (2°)

IR (KBr cm$^{-1}$): 3334, 3059, 3029, 2901, 2864, 2208, 1594, 1493, 1477, 1452, 1343, 1267, 1093, 755, 701

Specific rotation $[α]^{25}_D$=+82.9 (c 1.02, CHCl$_3$)

Melting point: 52°-54° C.

MS (APCI) m/z 563 (M-H)$^-$

From the above results, the optically active compound represented by the formula (II) was obtained from (S)-(+)-mandelic acid in an overall yield of 8.5% through eight steps.

Next, complexation ability and enantiomer-recognizing ability of the optically active compound represented by the formula (II) were evaluated by using both enantiomers of 2-amino-1-propanol.

According to a titration experiment in CDCl$_3$ using the $^1$H-NMR spectrum, the stability constant for complexation at 25° C. is 61 M$^{-1}$ with (R)-2-amino-1-propanol, and 14 M$^{-1}$ with (S)-2-amino-1-propanol, and enantioselectivity as high as $K_R/K_S$=4.3 was observed. When titration was carried out in CHCl$_3$ using the UV-vis and fluorescence emission spectra, there were confirmed that the resulting ammonium phenolate salt-complex has absorption at about 330 nm, which is highly well overlapped with the fluorescent spectrum of the compound represented by the formula (II).

Therefore, it is anticipated that the stronger the complex formation, the larger the re-absorption, thereby amplifying selectivity. Therefore, the compound was excited at 312 nm, its isosbestic point, and its fluorescence intensity was observed at 340 nm, its maximum fluorescence wavelength. From its Stern-Volmer plot, $K_{SV}$ was obtained at 25° C. As a result, $K_{SV}$ is 6.6 M$^{-1}$ for (R)-2-amino-1-propanol, and 3.3 M$^{-1}$ for (S)-2-amino-1-propanol, the ratio being doubled. As described above, there was confirmed that the optically active compound represented by the formula (II) itself is capable of amplifying enantiomer-recognizing ability due to reabsorption of fluorescence emission by the complex.

As described above, there was confirmed that since the selectivity is amplified by synergistic functions of selectivity due to complex stability with both enantiomeric amines and selectivity as a quenching agent of the complex formed by the enantiomeric amines, the optically active compound of the present invention represented by the compound represented by the formula (II) can serve as a chiral sensor having a high enantioselectivity.

INDUSTRIAL APPLICABILITY

Since the optically active compound of the present invention is capable of highly selectively recognizing a specified chiral compound in high sensitivity, the compound is very useful as a chiral sensor for practical purposes.

The invention claimed is:

1. An optically active compound having an unsaturated bond at an optically active binding site, wherein the unsaturated bond and a fluorescent substituent or a substituent capable of imparting fluorescence are united in a conjugated manner, wherein the compound is represented by the formula (I):

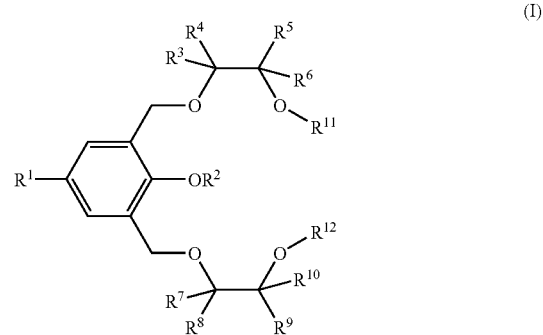

wherein R$^1$ is an aromatic ethynyl group; R$^2$ is a hydrogen atom or an alkyl group having 1 to 10 carbon atoms; each of R$^3$, R$^4$, R$^5$, R$^6$, R$^7$, R$^8$, R$^9$ and R$^{10}$ is independently a hydrogen atom, or an alkyl group having 1 to 30 carbon atoms, a cyclic alkyl group having 3 to 30 carbon atoms or an aryl group having 6 to 30 carbon atoms, each of which may have a substituent, with proviso that each of R$^4$ and R$^5$, and R$^8$ and R$^9$ may be bonded to form an alkylene group having 2 to 60 carbon atoms; and each of R$^{11}$ and R$^{12}$ is independently a hydrogen atom or an alkyl group having 1 to 15 carbon atoms which may have a hetero-atom, with proviso that R$^{11}$ and R$^{12}$ may be bonded to form an alkylene group having 2 to 30 carbon atoms which may have a hetero-atom.

2. A chiral sensor comprising the optically active compound as defined in claim 1.

* * * * *